(12) United States Patent
Peyton et al.

(10) Patent No.: US 7,267,774 B2
(45) Date of Patent: Sep. 11, 2007

(54) FUEL AND BY-PRODUCTS FROM FERMENTATION STILL BOTTOMS

(75) Inventors: Thomas O. Peyton, Lafayette, IN (US); Birgitte Kiaer Ahring, Hoersholm (DK); Lars Erik Rohold, Odense (DK)

(73) Assignee: NouvEau Inc., Lafayette, IN (US)

( * ) Notice: Subject to any disclaimer, the term of this patent is extended or adjusted under 35 U.S.C. 154(b) by 224 days.

(21) Appl. No.: 11/127,670

(22) Filed: May 12, 2005

(65) Prior Publication Data

US 2005/0252858 A1 Nov. 17, 2005

Related U.S. Application Data

(60) Provisional application No. 60/570,935, filed on May 13, 2004.

(51) Int. Cl.
*C02F 3/28* (2006.01)
*C02F 11/04* (2006.01)
*C02F 103/32* (2006.01)
*B01D 61/00* (2006.01)

(52) U.S. Cl. ............... 210/603; 210/641; 210/650; 210/652; 210/259; 203/DIG. 25

(58) Field of Classification Search ............... 210/603, 210/641, 649, 650, 652, 252, 259; 203/DIG. 25
See application file for complete search history.

(56) References Cited

U.S. PATENT DOCUMENTS

| | | | |
|---|---|---|---|
| 3,040,060 A | 6/1962 | Kulik | |
| 3,784,457 A | 1/1974 | Mizutani et al. | |
| 4,001,198 A | 1/1977 | Thomas | |
| 4,959,237 A | 9/1990 | Walker | |
| 5,032,265 A * | 7/1991 | Jha et al. | 210/195.2 |
| 5,177,008 A * | 1/1993 | Kampen | 435/139 |
| 5,250,182 A | 10/1993 | Bento | |
| 5,374,356 A | 12/1994 | Miller | |
| 5,536,325 A | 7/1996 | Brink | |
| 5,773,526 A | 6/1998 | Van Dijk | |
| 6,036,854 A | 3/2000 | Potter | |
| 6,187,196 B1 | 2/2001 | Way et al. | |
| 6,368,849 B1 | 4/2002 | Norddahl | |
| 6,423,236 B1 | 7/2002 | Shiota et al. | |

FOREIGN PATENT DOCUMENTS

JP  2005-296414  * 10/2005

* cited by examiner

*Primary Examiner*—Fred G. Prince

(57) ABSTRACT

The disclosed invention is an improved method for treating ethanol distillation still bottoms by recovering, through solids separation and pressurized membrane filtration, potable water from still bottoms for human consumption by bottling or for reuse, and concentrating the solids with beneficial properties recovered such as chemicals, nutrients and medicinals before anaerobic digestion. The invention is on improved process because it can reduce the volume of solids to manage, recovers the water from the fermentation still bottoms while pasteurized, maintains the chemical and physical properties of solids for beneficial property recovery, improves ethanol and energy efficiency, and results in clean discharge to the environment including carbon dioxide recovery. A bioreactor produces a gas rich in methane fuel from the concentrate to power the pressurized filtration process and an aqueous ammonia solution to recover or recycle. This invention improves environmental quality, conserves energy, and produces a beverage water for bottling that can be of an organic origin with reliable source and quality.

30 Claims, 2 Drawing Sheets

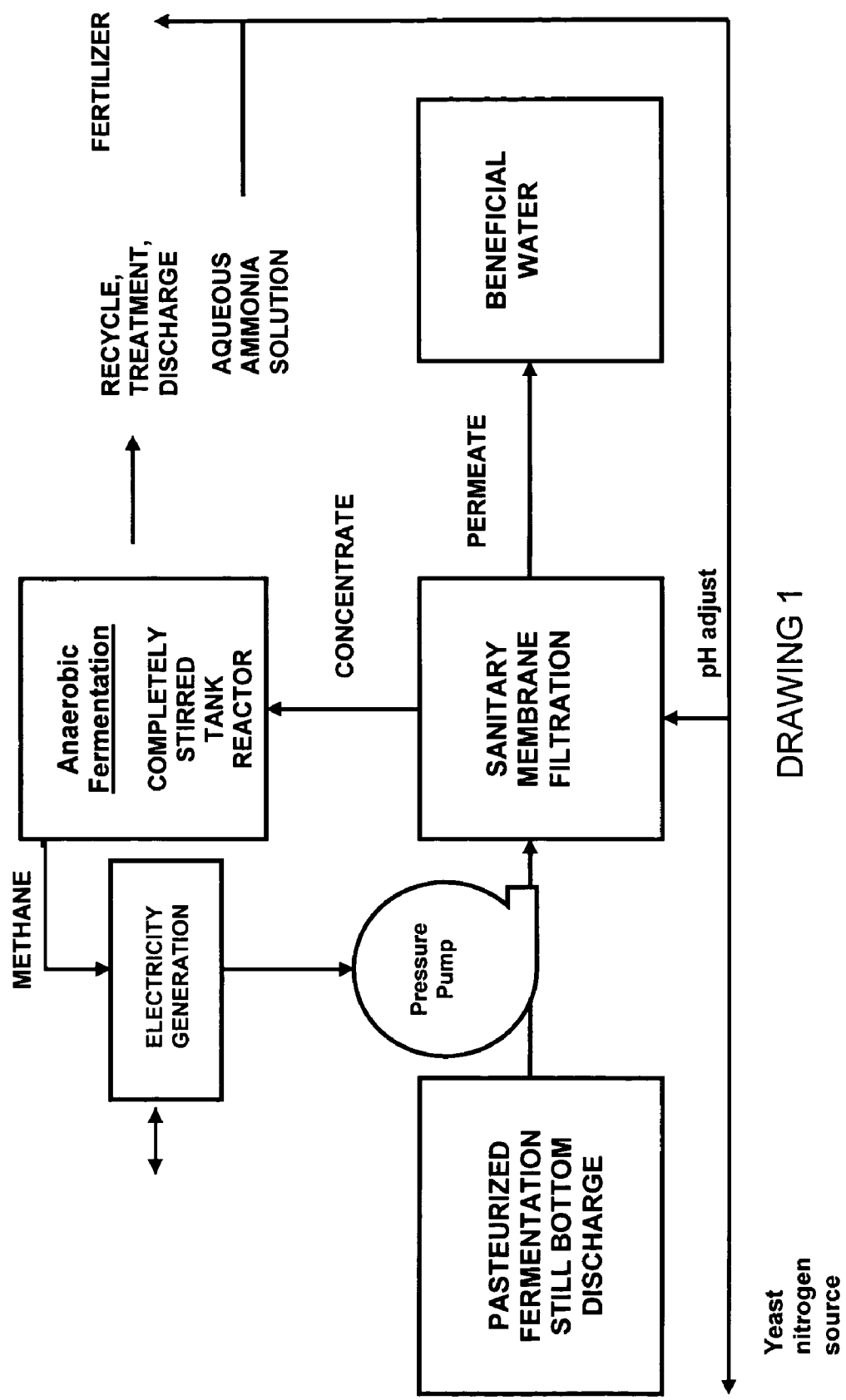
DRAWING 1

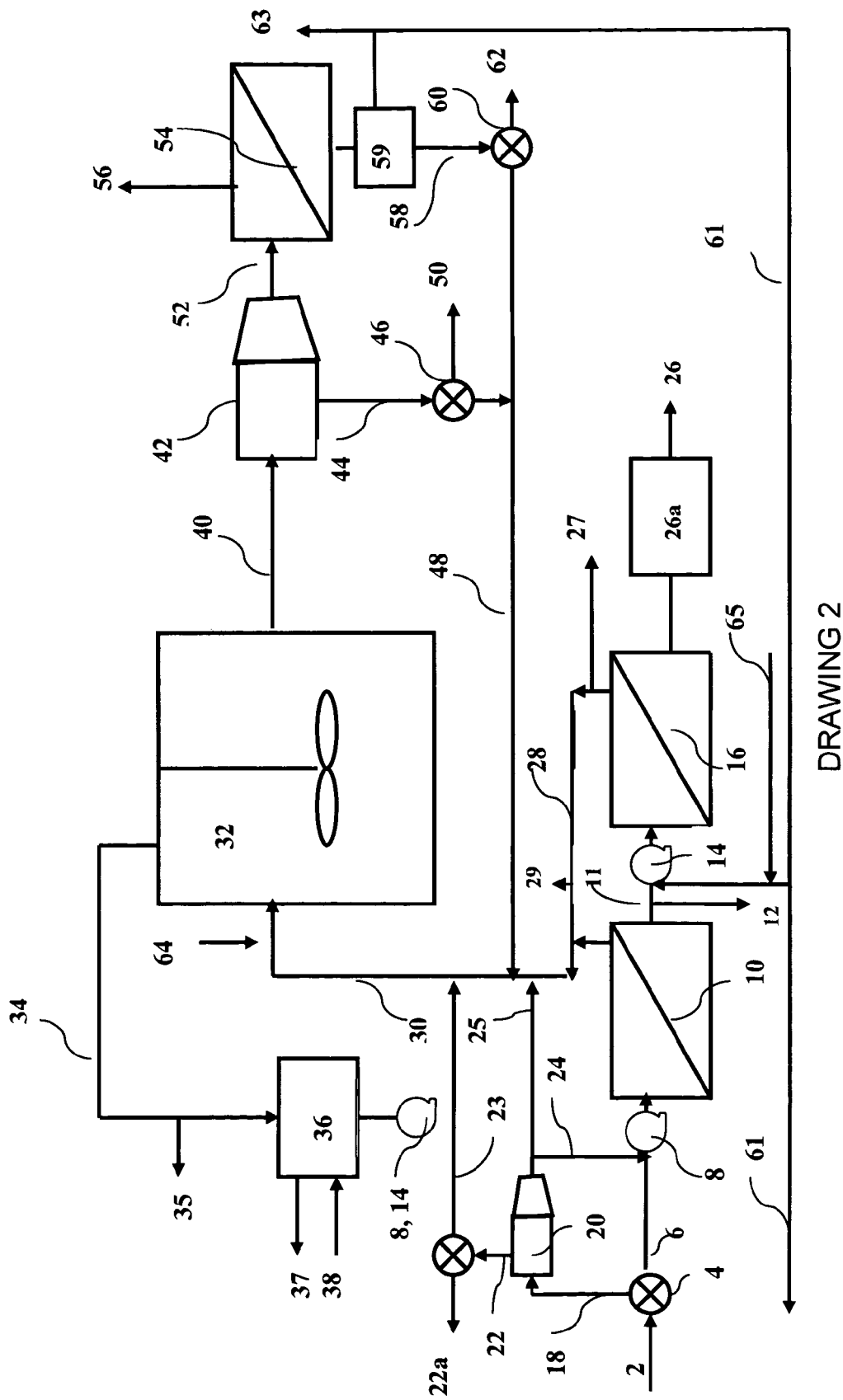
DRAWING 2

FUEL AND BY-PRODUCTS FROM FERMENTATION STILL BOTTOMS

CROSS-REFERENCE TO RELATED APPLICATIONS

This application claims the benefit of provisional patent application Ser. No. 60/570,935, filed May 13, 2004 by the present inventors.

FEDERALLY SPONSORED RESEARCH

Not Applicable

SEQUENCE LISTING OR PROGRAM

Not Applicable

BACKGROUND OF THE INVENTION

1. Field of the Invention

The disclosed invention relates to an improved method for treating ethanol fermentation still bottoms and recovering useful products there from. More specifically, this invention advantageously separates the discharged yeast fermentation solid and liquid residues while pasteurized by pressure across membrane filters in sanitary conditions with the permeate retaining low molecular weight minerals and nutrients at low to almost no concentration to make a unique non-alcoholic beverage or clean water for reuse in the process. Further, the means is unique and advantageous for the still bottom solids to be simultaneously concentrated at a high temperature for anaerobic digestion in a continuously stirred tank reactor operated at thermophilic conditions thereby efficiently liquefying the organic solids producing a gas rich in methane to supply more than enough fuel to power the pressurized filtration and an aqueous ammonia liquid recovered to supply nitrogen for yeast cultivation prior to alcohol fermentation or to adjust the pH with other alkali before reverse osmosis. In this process, the volume of waste discharge managed from anaerobic digestion is >50% less than had it not been concentrated before digestion.

2. Prior Art

Most of the 4000 alcohol distilleries in the world use starch and sugar feedstock up to 20% concentration in water for ethanol yeast fermentation that is heated to boiling in a still to evaporate the volatile fermentation products, mostly azeotropic ethanol, that condense in a column separator and the residuals are discharged as hot still bottoms that can contain from 2-10% inorganic and organic dissolved and suspended solids composed mostly of spent yeast cells and cell parts, metabolites, fermentation by-products, and non-fermentable starch and sugar feedstock residues. Nitrogen is often added to culture yeast before fermentation and typical yeast is composed of nearly 90% protein and carbohydrates. Following distillation this distilled fermentation water is often discharged directly to a water course, decanted into heavier and lighter fractions, or is evaporated to recover the solids as animal feed, filtered to recover other fermentation by-products from a concentrate, or biologically treated by anaerobic digestion to recover methane fuels. There are no unit methods known or found in the related art where discharged still bottoms are filtered in their pasteurized state under sanitary conditions with the water and nutrients directly recovered for beneficial human consumption while the solid concentrate is conveyed to a anaerobic bioreactor that recovers methane to power the pressurized membrane filtration in an energy efficient process.

Pressure filtrations are most frequently used in the agricultural and food processing industry to concentrate solid and separate liquid fractions through porous membranes. For example, in U.S. Pat. No. 4,959,237 by Walker, a series of reverse osmosis units are used to concentrate fruit juice to improve the product quality and in U.S. Pat. No. 4,001,198 by Thomas, ultrafiltration is used to concentrate and pasteurize cheese whey nutrients. In Walker's invention, the permeate is recycled back to reverse osmosis and in Thomas' invention the permeate is discharged. In neither case is the permeate used as potable water and pasteurization is required in Thomas' to maintain sanitary condition of the concentrate. In U.S. Pat. No. 5,250,182, Bento et al invent a plurality of membrane based processes to recover lactic acid and glycerol from a corn thin stillage stream following industrial ethanol fermentation and distillation that obviates the need for evaporation to concentrate syrup and produce lactic acid-free and glycerol-free animal feed upon drying with a filtration permeate that produces mineral free water to recycle as makeup water to the ethanol fermentation zone or as boiler water make-up. Bento et al's light stillage filtration invention means not to produce methane through anaerobic fermentation of the concentrate for an energy efficient pressurized filtration and means not to produce a nutrient water under sanitary conditions from pasteurized permeate for human consumption.

Ultrafiltration separates particles sized between 0.1 to 0.005 microns, nanofiltration separates particles between 0.005 and 0.001 microns, and reverse osmosis separates particles that are smaller than 0.001 microns. Generally, ultrafiltration has a molecular weight cutoff of 10,000 Daltons, nanofiltration 700 Daltons and reverse osmosis a molecular weight cutoff of 50-100 Daltons. Pressurized membrane assemblies can be tubular, hollow-fiber, spiral-wound, or flat plate with inlet pressures 40 bars or greater most often used. Membranes for use at high temperatures are manufactured of the polyamide type.

As disclosed in the treatment of a sugar and starch wastewater, U.S. Pat. No. 6,036,854 to J. Potter, a concentration process using ultrafiltration is positioned at the front of a treatment system to convey the concentrates to a mixing tank for hydrolyzing the starch to sugars and adding nutrients to form a feedstock to a fermentation tank that grows yeast cells. However, the permeate from the ultrafiltration is discharged to the sewer and is not beneficially used and there is no methane fermentation for energy recovery to power the pressurized ultrafiltration system from the concentrate.

As disclosed in U.S. Pat. No. 6,423,236 to Shiota, et al., a reverse osmosis system is used following wet-oxidation of organic wastewaters at high temperatures to separate molecules into the concentrate stream with acetic acid salts preferentially being the molecular weight of the concentrate cut off produced in the energy intensive wet oxidation process. In the preferred embodiment, Shiota, et al., suggest food processing wastes among many others as one possible organic source, option for elimination of wet-oxidation, and a non-descriptive anaerobic fermentation of the concentrate and household water use of the permeate from the reverse osmosis system. However, Shiota et al., make no specific claims to anaerobic fermentation or type in their invention, use of any methane gas to power the pressurized filtration system, recovering ammonia from the anaerobic fermentation to adjust pH before reverse osmosis, claim a temperature of 40 Celsius or below in reverse osmosis and a minimum concentration of 30 weight percent of an oxidizable substance as feedstock. For pasteurization to be in effect (70 Celsius for 30 minutes) would require a hot wet oxidation pre-treatment of this concentrated waste using the Shiota et al process before separation by reverse osmosis. Shiota, et al., therefore do not address the combined conditions necessary to separate fermentation still bottoms or many other similar food processing wastes by ultrafiltration or reverse osmosis before anaerobic digestion and to treat the concentrate by anaerobic digestion to recover energy to produce potable water for human consumption. The Shiota et al., process is disadvantageous to still bottom discharges because its descriptive specifications of concentration and temperature thresholds do not match those of fermentation still discharges or specific anaerobic fermentation processes and it would not be cost effective to adjust those parameters by further concentration, dilution and cooling not specified or disclosed.

Conventioanl anaerobic fermentation to produce methane gas is a mixed culture microbial process of liquefaction, acidogenisis and methanogenisis. Shiota et al., is using an energy intensive physical chemical process of wet-oxidation of organic wastewaters followed by reverse osmosis and is not descriptive of and is deficient in the specifications for a pressurized filtration system before anaerobic digestion to separate solids and liquids in an energy efficient and sanitary process without wet-oxidation.

Methanogenic bacteria are strictly anaerobic and die in the presence of oxygen. Unlike aerobic bacteria that convert its feedstock into microbial biomass and carbon dioxide through oxygen respiration, anaerobic bacteria convert its feedstock primarily into methane gas by a metabolic transfer of hydrogen. Methanogenisis is descriptive of an efficient biofuel cell process. Conventional anaerobic fermentation of concentrated organic wastes, particularly fermentation distillery discharges, use a variety of methods to increase the rate of degradation in order to decrease the size of the reactor and improve efficiency. Liquefaction (hydrolysis) and methanogenisis are rate limiting when performed together and hydraulic retention times toward 20 days and loading rates much less than 10 kg COD/cubic meter-day are often required for the mixed bacterial cultures to work efficiently in harmony together. Because the methanogenic bacteria are slow in reproductive growth rates and are sensitive to pH, they are most often rate limiting in the presence of an excess of fermentable acids, such as acetic and proprionic acids. For example, if hydrolysis occurs more rapidly than the slower methanogenisis, a build up of acidic conditions can occur and destroy the methanogenic bacteria. On the other hand, if the waste contain recalcitrant organics, hydrolysis will occur slowly limiting the feedstock for the methanogenic process. Various process control factors are used to improve efficiency of methanogenisis, including increasing mean cell residence times, separating hydrolysis and acidification from methanogenisis and increasing reaction rates by increasing temperatures that in turn culture a different and more efficient mixed bacterial culture.

Anaerobic lagoons, continuously stirred tank reactors (CSTR), CSTR's operated in contact mode, anaerobic filters, upflow anaerobic sludge blanket reactors (UASB), anaerobic fluidized bed reactors, and expanded bed reactors are among the technologies used for the distillery industry. The UASB reactor enhances reaction rate by increasing mean cell residence times by recirculating within the reactor granular particles and bacterial flocs that float on the surface that separates the reaction locations of acidification (5 days) and methanogenisis (7 days) in the reactor (see U.S. Pat. No. 5,773,526, Van Dijk, et al). The UASB method is sometimes dependent on preventing interfering flocs and too high of a strength of organic and suspended solids can inhibit reactions, often times requiring dilution. Though studied to operate in thermophilic mode (50-65 Celsius), reaction rates tend to be greater and interfere with floc formation. UASB systems are frequently used on distillery wastewaters and research has shown loading rates when operating in thermophilic mode of 16 kg of COD per cubic meter-day with 90% destruction for cane sugar distillery discharges. UASB systems can not operate at high suspended solids loadings.

CSTR reactors are conventional anaerobic digesters for high suspended solids loading and the hydraulic and mean cell residence times are about the same. The mean residence time of the cells can be increased by separating cells from discharge and recirculating in contact mode. Studies of high concentration agricultural wastes operating in thermophilic contact mode at 8 day retentions have shown loading rates of 9 kg COD/cubic meter-day with 75% destruction and improved performance in thermophilic over mesophilic in destroying COD and enhancing the rate of liquefaction and methanogenisis.

Compared to a CSTR system that doubles the solids concentration before anaerobic digestion, the UASB system exposes over 50% more water to bacterial degradation and consequently discharges a much greater volume from the digester for waste management.

Pressurized membrane systems are used to refine and produce drinking water from wastewater. In U.S. Pat. No. 6,368,849, Norddahl invents a CSTR anaerobic fermentation process that recovers energy to power an ultrafiltration and denitrification device. Norddahl's ultrafiltration device is placed after anaerobic bacteria consume organic wastes. This process is disadvantageous if applied to fermentation still bottoms for beneficial drinking water recovery because there would be no separation of the beneficial characteristics of the pasteurized still bottoms into the permeate before bacterial degradation and contact. Nitrogen is recovered as aqueous ammonia for use as a fertilizer. In U.S. Pat. No. 5,374,356 Miller et al invent a ultrafiltration and nanofiltration device for treating wastewaters, particularly gray water, in closed environments such as ships for conserving and recycling the permeate as potable water. The invention is disadvantageous as it means not to produce methane through anaerobic fermentation of the concentrate for an energy efficient pressurized filtration and means not to produce a potable water under sanitary conditions from pasteurized feedstock for human consumption.

Pressurized membrane systems are used to manufacture a water of beneficial character for commercial retail sales. The bottled water retail market is over $45 billion. There is a consumer demand for bottled water as a beverage because the source, process and composition is known and reliable and specific sealed and labeled sources containing nutrients or nutritious sources are more valuable to a health conscious consumer than bottled water from a generic source. Bottled water is frequently marketed and labeled as reverse osmosis or ultrafiltered water to gain acceptance that it has been treated and additives are often introduced to enhance nutritional value, color, odor and taste. With groundwater contamination, air pollution fallout and runoff into water bodies, spring water and river waters are becoming less reliable sources. There is a limited product on the market where pure beneficial water is obtained directly from the feedstock of a pasteurized source. Yeast and yeast extracts are frequently sold in dried solid concentrate in health food stores with natural protein and vitamins. There are limited, if any, beverages known on the market derived directly from the filtration of fermentation still bottoms.

3. Objects and Advantages

The objectives and advantages of our invention as discussed above in relation to the disadvantages of the prior art are numerous and several of the objects and advantages of the present invention are:

(a) to provide a unique process that separates under sanitary conditions the solid and liquid components of a nutrient rich pasteurized stream of fermentation still bottoms and converts the solid organic concentrate to methane fuels and collects the permeate as a nutrient rich or clean and clear fraction for human consumption as a beneficial water;

(b) to provide a pressurized filtration that maintains the pasteurized character of discharged still bottoms in a sanitary state to produce a beverage aseptically before any other process that might be septic;

(c) to provide a beneficial liquid product of yeast and yeast fermentable residues at predetermined molecular weight cutoffs providing a superior water product that is reliable, safe and appealing for human consumption with or without further refinement and additives;

(d) to provide a clean permeate water to be recycled into the pre-distillation fermentation process, as boiler makeup water, or discharged in volume and concentration as permitted acceptably into the environment;

(e) to provide filtration before anaerobic digestion to lessen the hydraulic load on a CSTR reactor and thus reduce the hydraulic volume of wastewater discharged from the CSTR reactor for subsequent waste management;

(f) to provide a method to produce a liquid ammonia solution from the anaerobic digestion process to recover as a fertilizer, to provide a nitrogen source to culture yeast before ethanol fermentation or used with other alkali to adjust pH of nanofiltration permeates to recover ammonium salts from reverse osmosis concentrates;

(g) to provide a process to pressure filter before anaerobic digestion to produce a less solids concentrated and diluted permeate stream allowing such stream to be treated by a UASB or similar anaerobic process to produce fuel value methane gas;

(h) to provide a process to pressure filter before anaerobic digestion to increase the solids concentration to more optimal conditions for a CSTR reactor;

(i) to provide a total process operated above 50 C that conserves the heat entropy of the discharge to operate pressure filtration in a pasteurized state and CSTR anaerobic fermentation at thermophilic temperatures;

(j) to provide a in line process to pressure filter before anaerobic digestion to recover sanitary pasteurized beneficial water and returning separated solids to be diluted with makeup water for treatment by a UASB or similar fermentation process to produce fuel value methane gas;

(k) to provide a process to filter before anaerobic digestion with means for converting the concentrated solid organics to produce methane gas of a fuel value to power the pressurized filtration system and other energy systems within and outside the process;

(l) to provide a process to reduce the volume of the reactor by operating in a thermophilic temperature range that increases degradation rates and also advantageously settles or separates the solids from the anaerobic discharge to allow 1) efficient return of active cells to the anaerobic fermentation process to increase mean cell residence time and further increase degradation rates and, 2) to collect said anaerobic discharge solids to apply to land as a nutrient compost;

In addition, further objects and advantages among many others are to provide a process which produces a safe and reliable higher value added water product for human consumption making the process more economical and advantageous as an asset compared to wastewater treatment of fermentation still bottoms per se' that are generally looked upon as a financial liability to the generator who is unable to otherwise quantify the economic value of the treatment process.

SUMMARY OF THE INVENTION

In accordance with the present invention a method is provided to make clean water and a non-alcoholic beverage directly from yeast fermentable still bottoms through a pressurized filtration process that also concentrates solids for anaerobic digestion to recover methane fuel to power the process and other useful by-products. This process comprises the steps of: 1) filtering still bottoms that are discharged>70 C pasteurized through a plurality of pressurized semi-permeable membrane filters, commonly referred to as ultrafiltration, nanofiltration and reverse osmosis and collecting the permeated liquid fractions retaining low molecular weight minerals and nutrients at low to almost no concentration and: 2) conveying the filtration concentrate of the fermentation still bottom solids to thermophilic anaerobic fermentation where the more concentrated organic solids are biologically converted to methane gas that is recovered as fuel energy to power the membrane pressurization pumps and auxiliary and external processes. The anaerobic fermentation discharge is separated advantageously under thermophilic conditions with solids optionally returned to the process to increase mean cell residence time and the liquid stream denitrified to produce ammonia to recycle. Operated at thermophilic temperature (50C-65C) obviates the need for cooling when filtered at pasteurized temperatures (70C-100 C), and retains beneficial properties to both the permeate purification and anaerobic digestion process. Centrifugal decantation is a pre-separation of thick whole stillage to a thinner stillage to improve pressurized filtration of the liquid stream.

BRIEF DESCRIPTION OF THE DRAWING

Drawing 1 is a conceptual diagram of the method for treating still bottoms in the embodiment of the present invention.

Drawing 2 is a schematic diagram of the method for treating still bottoms in the embodiment of the present invention.

DETAILED DESCRIPTION—DRAWING 1 AND 2—PREFERRED EMBODIMENT

Referring now to the drawings there is shown a conceptual diagram of the preferred embodiment of the process and system Drawing 1 for still bottom treatment to recover fuel and beneficial water in accordance with the present invention and a specific schematic diagram Drawing 2 of the method. As shown a discharge stream 2 of still bottoms is issued from an alcohol fermentation and distillation facility, not shown, at temperatures greater than 70 C and less than 100 C constituting a pasteurized state, through appropriate piping. Though not necessarily captured within this temperature range, the discharge should be maintained sanitary and preserve the characteristics of the spent yeast cells and cell parts, metabolites, fermentation byproducts, and non-fermentable starch and sugar feedstock residues without biological degradation or microbial contamination. Starch and sugar feed stocks can consist of any type of fermentable carbohydrate in the presence of an ethanol producing yeast strain. These starch and sugar feedstocks can include molasses, cane sugar, corn starch, barley, other grains such as rice, and fruits such as grapes and grape skins, and cellulose broken down to sugars through physical chemical and enzymatic processes, and starch converted to sugars with amylase. Other hot organic wastes that are not from still bottoms but meet these characteristics, such as discharges from high temperature processing of food products can also be a feedstock. The preferred solids concentration of spent yeast cells and cell parts, metabolites, fermentation byproducts, and non-fermentable starch and sugar feedstock residues in the still bottom discharge may be a total solids concentration less than 10% w/w in water, more typically from 1% to 7%, with a COD concentration from 20,000 to 80,000 ppm. The specific rate of discharge will depend on the nature of the primary processing facility, but is typically on the order of at least 25,000 to 250,000 gallons per day or greater and at a temperature above 70 C.

The pasteurized still bottom stream 2 continues through a two-way valve 4 to stream 6 where it is pressurized 8 to between 15 and 40 bar and enters a ultrafiltration-nanofiltration assembly 10 with predetermined molecular weight cutoff of 700 to 10,000 Daltons where the concentrate 28 is conveyed to line 30. The pasteurized stream in its preferred embodiment is first filtered at an inlet temperature between 70-80 C although filtration can occur between 35-70 C when sanitary conditions are maintained.

When the discharge is a "heavy stillage" that can foul pressurized membrane filtration or has a coarse suspended solid that has other by-product value such as distillers dried grain, the heavy stillage is directed by the two-way valve 4 to a centrifugal decanter 20 or other coarse solid-liquid separating device and separated into thick 22 and thin 24 fractions with a predetermined amount of the thick fraction to be recovered as a by-product by line 22a such as distillers dried grain and through line 23 by-passing pressurized filtration to enter line 30. The thin fraction in line 24 returns to the main stream 6 before pressurized filtration less a predetermined fraction that is between 0.0 and 0.9 directed by line 25 to line 30.

The ultrafiltration-nanofiltration (UF-NF) assembly have spiral wound membrane filters although other membrane filters can be used, and in its preferred embodiment of pasteurized inlet temperature>70 C is of a polyamide type filter, and has a predetermined molecular weight cutoff between 700 to 10,000 Daltons so that the permeate 11 generally has molecules from the still bottoms that are below this predetermined size. The UF-NF permeate withdrawn in whole or in part at this stage 12 of filtration is discharged to the environment, is treated by aerobic or anaerobic processes (see U.S. Pat. No. 5,773,526 for example), returned to the process, or recovered for beneficial uses.

The UF-NF permeate remaining is neutralized to a predetermined pH level between 4 and 7.5 by addition of an alkali consisting of a liquid sodium, calcium and ammonium salt solution for pH adjustment line 65, repressurized 14 to 20-50 bar to flow into the reverse osmosis (RO) filtration assembly 16 where the concentrate with a molecular weight greater than 50-100 Daltons is passed to line 28. Line 27 withdraws the RO concentrate to recover beneficial properties of the fraction greater than 50 to 100 Daltons at the predetermined cutoff of the UF-NF filter. The RO assembly have spiral bound membrane filters although other membrane filters can be used. In its preferred embodiment of pasteurized inlet temperature >70 C the filter is of a polyamide type. The RO permeate 26 is clean beneficial water for human consumption or other beneficial uses and is processed directly from the pasteurized still bottoms without additives other than pH adjustment. In its preferred embodiment when operating at outlet temperatures 55-65 C. this RO permeate passes through a plurality of predetermined finishing steps 26a consisting of a) heat exchanger to cool to 25-30 C for bulk handling and the heat exchanged back to the process, and b) activated carbon, e) aeration, or d) vacuum degasification to remove unwanted gases. From 50-70% of the inlet volume to the pressurized filtration assembly is converted to a beneficial distillers water in this process. the product a highly marketable grade drinking water.

The combined concentrate from the UF-NF-RO pressurized filtration assembly in line 28 is 2-5 times the initial concentration of total solids (TS) in the still bottoms but should be limited to a predetermined level between 10-25% TS in line 30. In its preferred embodiment the concentrate in line 30 is at a temperature between 50-65 C but can be 25-50 C. Line 28 enters line 30 that enters an anaerobic fermentation tank 32 and in its preferred embodiment is a completely stirred tank reactor (CSTR) operating within thermophilic temperature range of 50-65 C, although it can be operated in a mesophilic temperature range of 30-40 C with lesser efficiency. To maintain TS concentration at a predetermined level between 10-25% TS when entering the CSTR, line 30 can also receive thick 23 and thin 25 stillage, recycled water and bacterial cells from the anaerobic fermentation discharge 48, and makeup water from an outside source 64. To also maintain the concentration in line 30 at the predetermined acceptable level between 10-25% TS, the concentrated permeate is additionally withdrawn from line 29 to reduce the line 30 concentration, and this withdrawn concentrate is for use other than fuel production in anaerobic fermentation (see U.S. Pat. No. 6,036,854 for example), or to blend with line 22a to supplement distillers dried grain (see (U.S. Pat. No. 5,250,182 for example) or beneficial properties recovered for other uses such as industrial, medicinal, nutrittional, or commercial chemical products.

In the preferred embodiment the loading rate to the thermophilic CSTR is at a predetermined level between 5-10 kilograms COD per cubic meter per day (kg/m3-d) and the reactor adjusted in volume and number of reactors to accommodate the influent COD level, with a minimum of two reactors operated in parallel. The reactor should be optimally designed at a predetermined hydraulic retention time between 15-25 days however adjustments can be made to allow for toxic interferences such as ammonia and sulfides. The CSTR process is a conventional anaerobic fermentation method and continuously stirs the concentrate. Methanogenic bacteria generating methane gas and other gases such as carbon dioxide and hydrogen sulfide are exhausted from the reactor 34 where the hydrogen sulfide is removed by conventional desulphurization processes with the resulting fuel gas of moderate energy value of 600-750 btu/ft3. The carbon dioxide is optional for removal but in the preferred embodiment the methane with carbon dioxide is converted to electricity 36 in a gas turbine or by other means with the electricity used to power the pressurized filtration process and the net electricity balance used to power auxiliary systems 37 within the process, in the fermentation distillery plant, or transferred to a utility supply grid. The fuel gas can also be conveyed 35 to another energy conversion process, such as boiler fuel, and the pressurized filtration process operated independent of fuel gas production by use of an outside fuel source or electricity supply 38.

The liquid discharge from the CSTR anaerobic fermentation 40 is conveyed to a centrifugal decanter 42 where it is separated into a solid stream 44 and liquid stream 52. The solid stream contains the majority of bacterial cells and non degraded suspended solids and a predetermined amount is divided by a two-way valve 46 into a return line 48 to the CSTR fermenter and the remaining 50 to a landfill as a compost. The liquid stream from the centrifugal decanter can be disposed of directly or denitrified (see U.S. Pat. No. 6,368,849) but in the preferred embodiment it is first pressure filtered by nanofiltration 54 where the concentrate 56 is a thick fluid and disposed in a sewer or hauled to a sewage treatment plant. The permeate stream 58 is primarily dissolved inorganic and organic solids including ammonia and undergoes denitrification 59 and recovery consisting of a) aqueous ammonia solution as fertilizer 63, b) return to the process as nutrient for yeast culturing and as an alkali to adjust the pH of the permeate input to reverse osmosis by line 61. An alkali other than aqueous ammonia solution can be supplied to adjust the pH of the permeate input to reverse osmosis by line 65. Following denitrification, a predetermined amount of the permeate stream is divided by a two-way valve 60 into the return line 48 as makeup water to the CSTR fermenter and the remaining 62 to an outside receiver.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which fall within the purview of the subject invention.

We claim:

1. Means for separating by centrifugal decantation before pressurized filtration the solid and liquid portions of the soluble and insoluble organic and inorganic still bottom discharge from ethanol fermentation distillation and separately conveying each said liquid and solid at predetermined volumes to a concentrate line for anaerobic digestion and remainder of said liquid portion to a pressure filtration line to further separate solids and liquids.

2. A potable water product from ethanol fermentation still bottoms through a process to separate still bottom liquid from solid organic and inorganic components while pasteurized by a sequence of steps that continuously subjects the still bottom liquid to steps that further separate organic and inorganic concentrate fractions of solids of lesser molecular weight from the liquid, wherein the separated solid concentrate fractions are anaerobically digested, the sequence of steps consisting of centrifugal decantation, pressurized ultrafiltration and nanofiltration to produce a filtration permeate through semi-permeable membranes with predetermined molecular weight pore sizes no more than 10,000 Dalton and no less than 700 Dalton, adjustment of pH of the filtration permeate to a predetermined level, pressurized reverse osmosis through a semi-permeable membrane of a molecular weight pore size between 50-100 Dalton producing a clear potable liquid that is finished to render the potable water product of low molecular weight solids of still bottoms used fur recycling, discharge, or human consumption by bulk handling or bottling.

3. The process in claim 2 wherein pressurized ultrafiltration, nanofiltration and reverse osmosis occurs at inlet pressures of 20-50 bar in spiral-wound filtration assemblies.

4. The process in claim 2 wherein the still bottoms are pasteurized and pressure filtered at temperatures between 25-80 C and said semi-permeable membrane filters for pressure filtration and reverse osmosis are of a polyamide type when temperatures of filtration are greater than 65 C.

5. The process in claim 2 wherein the filtration permeate from nanofiltration is adjusted with an alkali to neutralize organic acids at a predetermined pH between 4.0 and 7.5 before pressurized reverse osmosis.

6. The process in claim 2 wherein the filtration permeate from ultrafiltration-nanofiltration is anaerobically treated in an upflow anaerobic sludge blanket reactor.

7. The process in claim 2 wherein a permeate from reverse osmosis is finished by either activated carbon, aeration, or vacuum degasification and cooled in a heat exchanger.

8. The process in claim 2 wherein a permeate from reverse osmosis is finished by adjustment to a neutral pH.

9. The process of claim 2 wherein a permeate from reverse osmosis is reused or discharged.

10. The process of claim 2 wherein the potable water product is handled in bulk or bottled for human consumption, as a distillers water.

11. The organic and inorganic concentrate fractions of claim 2 wherein total or separate fractions of solid organic concentrate is anaerobically digested including under thermophilic conditions above 50 C to liquefy insoluble organics to improve acidogenisis, hydrogen production efficiency and methanogenisis.

12. The anaerobic digestion of claim 2 wherein a methane gas of fuel value is produced and used to recover its energy and the methane is separated from gas of no fuel value and the enriched gas separately used for its energy value.

13. The organic and inorganic concentrate fractions of claim 2 wherein the total or separate fractions of organic solids is anaerobically digested to produce by a predetermined process a ammonia solution for use as a fertilizer, for recycling to the ethanol fermentation process as a nutrient for yeast culturing, as a buffering agent to neutralize acids following nanofiltration wherein the ammonia salts are recovered from the concentrate of reverse osmosis filtration.

14. The organic and inorganic concentrate fractions of claim 2 wherein clean water is separated from the concentrate following anaerobic digestion by a sequence of steps that continuously subjects the concentrate to steps that further separate fractions of solids of lesser molecular weight from the concentrate, the steps consisting of anaerobic digestion, centrifugation, and nanofiltration through a semi-permeable membrane with a molecular weight pore size no less than 700 Dalton, recovery of ammonia by a predetermined process from the permeate, the resulting product being clean water for reclamation, discharge, or reuse.

15. The organic and inorganic concentrate fractions of claim 2 wherein solids are separated from the concentrate following anaerobic digestion by a sequence of steps that continuously subjects the solid phase to steps that further separate fractions of solids of lesser molecular weight from the concentrate, the steps consisting of anaerobic digestion, centrifugation and nanofiltration through a semi-permeable membrane with a predetermined molecular weight pore size no less than 700 Dalton, with a predetermined fraction of the solid phase from centrifugation returned to the anaerobic digester and the remaining solid, with the concentrate from nanofiltration, conveyed to an outside receiver.

16. A potable water product from ethanol fermentation still bottoms through a process to separate still bottom liquid from solid organic and inorganic components while pasteurized by a sequence of steps that continuously subjects the still bottom liquid phase to steps that further separate organic and inorganic concentrate fractions of solids of lesser molecular weight from the liquid, wherein the separated solid concentrate fractions are anaerobically digested after beneficial properties recovered, the sequence of steps consisting of centrifugal decantation, pressurized ultrafiltration and nanofiltration to produce a filtration permeate through semi-permeable membranes with predetermined molecular weight pore sizes no more than 10,000 Dalton and no less than 700 Dalton, adjustment of pH of the filtration permeate to a predetermined level, pressurized reverse osmosis through a semi-permeable membrane of a molecular weight pore size between 50-100 Dalton producing a clear potable liquid that is finished to render the potable water product of low molecular weight solids of still bottoms used for recycling, discharge, or human consumption by bulk handling or bottling.

17. The process in claim 16 wherein pressurized ultrafiltration, nanofiltration and reverse osmosis occurs at inlet pressures of 20-50 bar in spiral-wound filtration assemblies.

18. The process in claim 16 wherein the still bottoms are pasteurized and pressure filtered at temperatures between 25-80 C and said semi-permeable membrane filters for pressure filtration and reverse osmosis are of a polyamide type when temperatures of filtration are greater than 65 C.

19. The process in claim 16 wherein the filtration permeate from nanofiltration is adjusted with an alkali to neutralize organic acids at a predetermined pH between 4.0 and 7.5 before pressurized reverse osmosis.

20. The process in claim 16 wherein the filtration permeate from ultrafiltration-nanofiltration is anaerobically treated in an upflow anaerobic sludge blanket reactor and the separated solid concentrate used to recover the beneficial properties and the resulting solids and liquids returned to anaerobic digestion or the process in claim 16.

21. The process in claim 16 wherein a permeate from reverse osmosis is finished by either activated carbon, aeration, or vacuum degasification and cooled in a heat exchanger.

22. The process in claim 16 wherein a permeate from reverse osmosis is finished by adjustment to a neutral pH.

23. The process of claim 16 wherein a permeate from reverse osmosis is reused or discharged.

24. The process of claim 16 wherein the potable water product is handled in bulk or bottled for human consumption, as a distillers water.

25. The organic and inorganic concentrate fractions of claim 16 wherein the beneficial properties of concentrates are recovered before anaerobic digestion and the separated non-beneficial concentrate returned to anaerobic digestion, beneficial properties of the fractions including distillers dried grain, distillers dried grain solubles, medicinals, chemicals, and nutrients.

26. The organic and inorganic concentrate fractions of claim 16 wherein total or separate fractions of solid organic concentrate is anaerobically digested including under thermophilic conditions above 50 C to liquefy insoluble organics to improve acidogenisis, hydrogen production efficiency and methanogenisis.

27. The anaerobic digestion of claim 16 wherein a methane gas of fuel value is produced and used to recover its energy value and methane is separated from gas of no fuel value and the enriched gas separately used for its energy value.

28. The organic and inorganic concentrate fractions of claim 16 wherein the total or separate fractions of organic solids is anaerobically digested to produce by a predetermined process a ammonia solution for use as a fertilizer, for recycling to the ethanol fermentation process as a nutrient for yeast culturing, as a buffering agent to neutralize acids following nanofiltration wherein the ammonia salts are recovered from the concentrate of reverse osmosis filtration.

29. The organic and inorganic concentrate fractions of claim 16 wherein nutrients, chemicals and medicinals of beneficial value are recovered from the concentrate before anaerobic digestion and non-beneficial separated solids returned to an anaerobic digester and beneficial solids returned to the potable water.

30. The organic and inorganic concentrate fractions of claim 16 wherein clean water is separated from the concentrate following anaerobic digestion by a sequence of steps that continuously subjects the concentrate to steps that further separate fractions of solids of lesser molecular weight from the concentrate, the steps consisting of anaerobic digestion, centrifugation, and nanofiltration through a semi-permeable membrane with a molecular weight pore size no less than 700 Dalton, recovery of ammonia by a predetermined process from the permeate, the resulting product being clean water for reclamation, discharge, or reuse.

* * * * *